United States Patent [19]

Whitley

[11] Patent Number: 5,310,646

[45] Date of Patent: May 10, 1994

[54] METHOD FOR THE DETECTION OF MUCOPOLYSACCHARIDE STORAGE DISEASES

[75] Inventor: Chester B. Whitley, Shoreview, Minn.

[73] Assignee: Regents of the University of Minnesota, Minneapolis, Minn.

[21] Appl. No.: 806,833

[22] Filed: Dec. 9, 1991

Related U.S. Application Data

[63] Continuation of Ser. No. 297,051, Jan. 17, 1989, abandoned, which is a continuation-in-part of Ser. No. 194,553, May 13, 1988, abandoned.

[51] Int. Cl.$^5$ .................. C12Q 1/00; G01N 21/75; G01N 21/00
[52] U.S. Cl. .................. 435/4; 435/805; 436/166; 436/169; 436/811; 436/815; 422/56
[58] Field of Search .......... 435/4, 805; 436/811, 436/815, 826, 166, 169; 422/56

[56] References Cited

OTHER PUBLICATIONS

J. Muenzer, *Adv. Pediatr.*, 33, 269–302 (1986).
V. Shih, "Toluidine Blue O Spot Test (Berry Spot Test)" and "Alcian Blue Spot Test", *Laboratory Techniques for the Detection of Hereditary Metabolic Disorders*, Chap. 5, 103–106; 109–118 (CRC Press).
H. Berry, *Clin. Biochem.*, 20, 365–371 (Oct. 1987).
R. Humbel and S. Etringer, *Rev. Roum. Biochem.*, 11, 21–24 (1974).
Bonsnes and Taussky, *J. Biol. Chem.*, 158, 581–591 (1945).
J. Widom and S. Edelstein, *Chemistry* (W. H. Freeman & Company: San Francisco, Calif.), 220–221 (1981).
K. Huang et al., *Clinica Chimica Acta*, 151, 141–146 (1985).
E. Berman et al., *Clin. Chem.*, 16, 886–890 (1971).
H. Berry, *Clin. Chem.*, 5, 603–608 (1959).
H. Berry and J. Spinager, *J. Lab. & Clin. Med.*, 55, 136–138 (1960).

T. Bitter and H. Muir, *Anal. Biochem.*, 4, 330–334 (1962).
R. Burlingame et al., *Clin. Chem.*, 27, 124–128 (1981).
N. Carson and D. Neill, *Arch. Disease in Childhood*, 505–513 (1962).
G. Coppa et al., *Helv. paediat. Acta*, 42, 419–423 (1987).
N. Di Ferrante, *Anal. Biochem.*, 21, 98–106 (1967).
R. Farndale et al., *Connective Tissue Research*, 9, 247–248 (1982).
O. Folin and H. Wu, *J. Biol. Chem.*, 38, 81–110 (1919).
E. Gold, *Anal. Biochem.*, 99, 183–188 (1979).
R. Hata and Y. Nagai, *Anal. Biochem.*, 52, 652–656 (1973).
J. Hobbs et al., *The Lancet*, 709–712 (Oct. 3, 1981).
D. Hsu et al., *Anal. Biochem.*, 46, 156–163 (1972).
K. Huang et al., *Clin. Chimica Acta*, 151, 147–156 (1985).
M. Jaffe, "Ueber den Niederschlag, welchen Pikrinsaure in normalem Harn erzeugt und uber eine neue Reaction des Kreatinins", 391–400 (1886).
C. Kodama et al., *Clin. Chem.*, 32, 30–34 (1986).
W. Krivit et al., *New England J. Med.*, 311, 1606–1611 (1984).
M. Lammi and M. Tammi, *Anal. Biochem.*, 168, 352–357 (1988).
A. Mestel et al., *Surgery*, 57, 795–799 (1965).
M. Moore, *University of Minnesota Med. Bull.*, 2–6 (Winter, 1987).

(List continued on next page.)

Primary Examiner—Michael G. Wityshyn
Assistant Examiner—Ralph Gitomer
Attorney, Agent, or Firm—Mechant, Gould, Smith, Edell, Welter & Schmidt

[57] ABSTRACT

A method for screening a patient for mucopolysaccharidoses is provided in which sample urine absorbed onto a porous sheet and dried is extracted with water. 1,9-dimethylmethylene blue dye reagent in buffer is added to the aqueous extract to produce a test solution which is assessed spectrophotometrically for color change indicative of mucopolysaccharidoses. The invention is particularly applicable to rapid and reliable mass screening and diagnosis of newborn infants.

10 Claims, 7 Drawing Sheets

OTHER PUBLICATIONS

K. Nanto-Salonen et al., *Clinica Chimica Acta*, 146, 111–118 (1985).
D. Newton et al., *Anal. Biochem.*, 62, 268–273 (1974).
G. Panin et al., *Clin. Chem.*, 32, 2073–2076 (1986).
C. Pennock et al., *Acta Paediat. Scand.* 62, 481–491 (1973).
L. Rosenfeld, *Clin. Chem. Acta*, 31, 263–269 (1971).
L. Rosenfeld, *Surgery*, 70, 378–384 (1971).
L. Rosenfeld et al., "Determination of 'Heparinoid' Substances in Urine with a Dye-Binding Technic," 317–321 (1961).
A. Ruggeri et al., *Arzneim.-Forsch./Drug Res.*, 35, 1517–1519 (1985).
J. Sabater et al., *Clin. Gen.*, 4, 260–263 (1973).
P. Sabiston et al., *Anal. Biochem.*, 149, 543–548 (1985).
P. Sampson et al., *Anal. Biochem.*, 151, 304–308 (1985).
C. Scriver, "Screening Newborns for Hereditary Metabolic Disease", 807–821 (1965).
C. Scriver et al., "Population Screening: Report of a Workshop," *Prevention of Physical and Mental Congenital Defects, Part B: Epidemiology, Early Detection and Therapy, and Environmental Factors*, 89–152 (1965).
N. Seno et al., *Anal. Biochem.*, 37, 197–201 (1970).
J. Spranger, *Am. J. Med. Gen.*, 28, 489–499 (1987).
I. Staprans and J. Felts, *J. Clin. Investigation*, 76, 1984–1991 (1985).
K. Taylor and G. Jeffree, *Histochemical J.*, 1, 199–204 (1969).
P. Whiteman, *Biochem. J.*, 131, 351–357 (1973).
C. Whitley et al., *Birth Defects: Original Article Series*, 22, 7–24 (1986).
H. Berry et al., *J.A.M.A.*, 167, 2189–2190 (1958).
J. Rattenbury et al., *J. Clin. Pathol*, 41, 936–939 (1988).

METHOD FOR THE DETECTION OF MUCOPOLYSACCHARIDE STORAGE DISEASES

CROSS REFERENCE TO RELATED APPLICATIONS

This application is a continuation of U.S. application Ser. No. 07/297,051 filed Jan. 17, 1989, now abandoned, which is a continuation -in-part of U.S. application Ser. No. 07/194,553, filed May 13, 1988, now abandoned.

BACKGROUND

Mucopolysaccharide storage diseases or mucopolysaccharidoses (MPS) are lysosomal storage disorders that result from the deficiency of specific lysosomal enzymes. Currently, there are ten types of MPS. They differ in clinical features, accumulated storage materials and deficient enzyme. These storage diseases are characterized by intralysosomal accumulation of mucopolysaccharides, excessive urinary excretion of mucopolysaccharides, progressive mental and physical deterioration, and premature death. Patients are usually born without the visible clinical features of MPS, but develop progressive clinical involvement. Each type of MPS has a specific lysosomal enzyme deficiency with a characteristic degree of organ involvement and rate of deterioration. See Muenzer, *Adv. Pediatri.* 33:269-302(1986)

Known methods for the quantitative measurement and characterization of MPS are complicated and labor intensive. Generally urine specimens are first concentrated, dialyzed, or the mucopolysaccharide precipitated. The mucopolysaccharide is then identified and quantified by electrophoresis, by determination of uronic acid or by fractionation on a Sephadex column.

A number of screening tests for MPS exist. These tests can be divided into two types: metachromatic reactions of various dyes to glycosaminoglycans; and turbidity or precipitation tests with glycosaminoglycans interacting with acidified albumin solutions of quarternary ammonium compounds. Muenzer, supra. Several of the dye based procedures have been reduced to "spot" tests. These include: Toluidine Blue O Spot Test (Berry Spot Test) [*Laboratory Techniques for the Detection of Hereditary Metabolic Disorders,* Chp. 5:103–118 (CRC Press); Berry, *Clin. Biochem.,*20:365–71(1987)]; and Alcian Blue Spot Test [*Laboratory Techniques for the Detection of Hereditary Metabolic Disorders* supra.]. A qualitative colorimetric method using 1,9-dimethylmethylene blue on liquid urine samples to detect mucopolysaccharidosis in older children exhibiting physical abnormalities associated with MPS is also known. Humbel & Etringer *Rev. Roum. Biochem.,*11:-21-24(1974).

There are a number of drawbacks associated with existing MPS screening tests precluding their use for mass screening of children for MPS in the United States. Many paper spot tests give a high incidence of false-negative results. See Muenzer, supra. In the case of the Berry spot test, a high incidence of false positive is reported and fresh or frozen urine is required. The acid albumin gross turbidity test requires pure liquid urine and is relatively difficult, time consuming and expensive. Specifically, in the case of infants, liquid urine samples are time consuming and inconvenient to obtain and prepare, thus leading to higher costs. Many of the known mucopolysaccharide testing methodologies are inefficient in detecting all mucopolysaccharide disorders. One mucopolysaccharide disorder which is difficult to detect with certain existing methodologies is Morquio syndrome.

Accordingly, there is a need for an improved method to rapidly and accurately detect the presence of all MPS in urine without elaborate sample preparation and need to separate glycosaminoglycan from potentially intereferring substances (e.g., by chromatography) and which is also convenient with respect to the collection and preparation of small samples obtained from newborn infants and young children.

SUMMARY OF THE INVENTION

The present invention provides a rapid, specific and accurate quantitative assay for detecting the presence of mucopolysaccharide storage diseases, which is particularly amenable to presymptomatic screening and diagnosis of these conditions in newborn infants. Preferably, the test measures glycosaminoglycan in urine which has been dried onto a porous sheet, such as a filter paper sheet. Specific steps are employed to extract the dried sample, to apply a dye reagent standard (1,9-dimethylmethylene blue chloride, DMB) and to measure the concentration of glycosaminoglycan by spectrophotometric means. The concentration is then normalized to an internal standard, creatinine, and compared with the normalized concentrations determined for urine derived from control subjects. Normalization of these results to the urinary creatinine concentration is used to compensate for variations in urine concentration. The method of the present invention also provides a direct quantitative assay for mucopolysaccharide storage diseases in liquid urine using DMB.

In accordance with the present invention excessive urinary glycosaminoglycan can be quantified to screen for mucopolysaccharide diseases by a method comprising the steps of:

(a) extracting a sample of the patient's urine which has been absorbed onto a porous sheet and dried, by agitating said sheet with water for a period of time sufficient to yield an aqueous extract which contains glycosaminoglycan and creatinine;

(b) determining the amount of creatinine in a first portion of said aqueous extract, said amount of creatinine being normalized to standard creatinine reference solutions;

(c) adding a known amount of 1,9-dimethylmethylene blue chloride dye reagent to a second portion of said aqueous extract to produce a test solution, said test solution containing sufficient buffer to preclude precipitation of dye/glycosaminoglycan complexes;

(d) determining the amount of glycosaminoglycan in said test solution by inspection of color change in said test solution, said amount of glycosaminoglycan being normalized to a standard glycosaminoglycan solution;

(e) calculating urinary glycosaminoglycan in said sample as a ratio of normalized glycosaminoglycan to normalized creatinine; and (f) comparing the urinary glycosaminoglycan in said sample to control levels of urinary glycosaminoglycan.

As employed herein, the term "control level" refers to glycosaminoglycan levels which are representative of the glycosaminoglycan levels of a human subject of a specified age who is free of mucopolysaccharide disease, who excretes normal amounts of glycosaminoglycan. The range of normal newborn infants has been determined to be about 50–350 mg glycosaminoglycan/gm creatinine.

Pathologic evaluation of mg glycosaminoglycan/gm creatinine associated with MPS is generally greater than 350 mg glycosaminoglycan/gm creatinine. However, the lower end of the range of pathologic elevation can vary depending on patient age and particular form of mucopolysaccharide disorder. In certain cases glycosaminoglycan levels of patients exhibiting MPS disorders can be below 350 mg/gm creatinine; however, these cases may be associated with a sub-population having low base line normals.

DETAILED DESCRIPTION OF THE INVENTION

Figure 1:
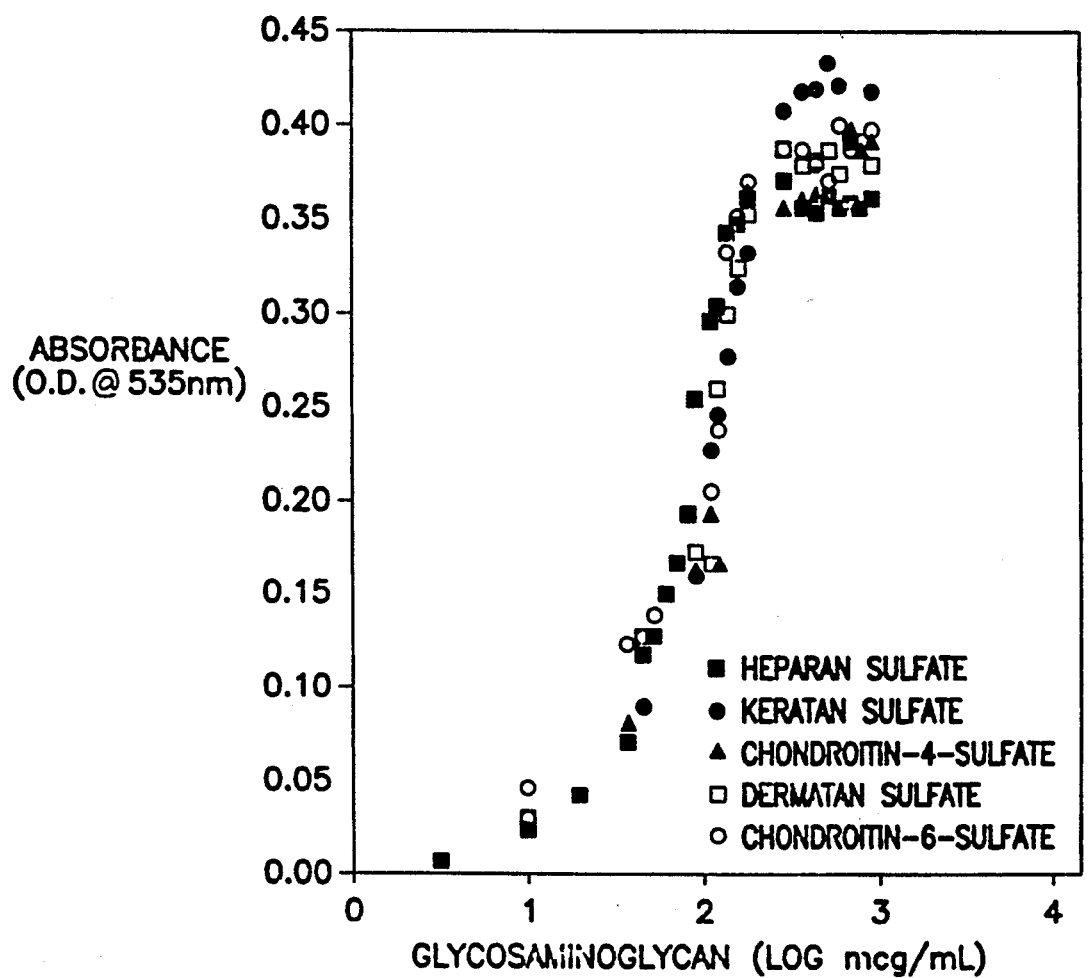
FIGS. 1 shows reactivity of glycosaminoglycan species with 1, 9-Dimethylmethylene Blue Dye.

The samples analyzed by the present method are urine samples which have been dried, preferably by evaporation under ambient conditions onto a porous, absorbent substrate sheet. The porous sheet can be made of any material, natural or synthetic, which will release at least the absorbed creatinine, and glycosaminoglycan upon extraction with water, without contaminating the aqueous extract with materials which can interfere with the spectrophotometric analysis. Preferred sheets include woven or non-woven, multi- or single-ply cellulosic sheets, e.g., filter paper, felt, paper toweling and the like.

In the case of children who are not toilet-trained, the sample is obtained by blotting a urine-soaked diaper with the absorbent sheet. In toilet-trained subjects, urine is collected and used to saturate the absorbent sheet. The wetted sheet is then dried on a clean surface under ambient conditions.

Extraction of Glycosaminoglycan and Urinary Creatinine (UCr)

A predetermined area of the dried sheet is isolated for analysis. For example, an about 20–40 cm$^2$ sheet of dried filter paper will generally provide a sufficient amount of sample. The paper and sample is agitated in the presence of an amount of water and for a period of time effective to extract the glycosaminoglycan and the creatinine therefrom. This period of time is typically between from about 20–40 minutes. The extraction is conducted so that the relative amount of the glycosaminoglycan to the creatinine in the final extract is essentially constant. An aliquot of the extract is isolated and creatinine measured by the method described in Bonsnes, Taussky on the colorimetric determination of creatinine by the Jaffee reaction. *J. Biol. Chem.*, 158:581–591 (1945), the disclosure of which is incorporated by reference herein.

A known amount of 1,9-dimeythlmethylene blue dye reagent is then added to a measured portion of the remainder of the aqueous extract to produce a test solution and reaction between the sample and dye is allowed to proceed. The test solution contains an amount of sodium formate buffer or similar other buffer, such as sodium acetate or citrate phosphate, effective to stabilize the dye complex test solution and preclude precipitation of glycosaminoglycan. Preferably, the buffer used is 0.05 M to 0.25 M sodium formate. Most preferably, about 0.2 M sodium formate buffer is employed. Reaction is complete in from about 3 seconds to about 30 minutes, and normally the test solution is allowed to react for at least 15 seconds. *Analysis of Samples by Spechrophotmetry*

The techniques of optical density spectrophotometry are employed to determine the level of glycosaminoglycan and 1,9-dimethylmethylene blue in a portion of the test solution. For a discussion of the general principles and parameters of optical density spectrophotometry, see J.M. Widom and S.J. Edelstein, *Chemistry* (WH Freeman & Co: San Francisco, CA), 220–221 (1981). The disclosure of which is incorporated by reference herein. Spectrophometry equipment for carrying out analysis of glycosaminoglycan levels are commercially available, Beckman, Instruments Inc., Irvine, CA.

Calculation of the amounts of glycosaminoglycan, and normalization of the amounts of the UCr concentration can be done manually, but preferably are done automatically after the run by a programmed computer. Calculation of the quantity of glycosaminoglycan, normalized by the UCr is calculated as follows:

$$\text{glycosaminoglycan/creatinine} = \frac{[(OD_{UGAG}) \times (\text{Slope}_{GAG})] + y\text{-intercept}_{GAG}}{[(OD_{UCr}) \times (\text{Slope}_{Cr})] + y\text{-intercept}_{Cr}}$$

where:
- $OD_{UGAG}$ = optical density of GAG-DMB test solution
- $\text{Slope}_{GAG}$ = slope of glycosaminoglycan standard curve, e.g., chondroitin-6-sulfate
- Y-intercept$_{GAG}$ = Y-intercept of glycosaminoglycan standard curve, e.g., chondroitin-6-sulfate
- $OD_{UCr}$ = optical density of creatinine test solution, per the method of Jaffee supra.
- $\text{Slope}_{UCr}$ = slope of creatinine standard curve, per the method of Jaffee supra.
- Y-intercept$_{UCr}$ = Y-intercept of creatinine standard curve, per the method of Jaffee supra.

Therefore, the measured glycosaminoglycan levels are expressed as mg glycosaminoglycan/gm creatinine and are compared to the appropriate control levels for individuals exhibiting normal glycosaminoglycan excretion. A test was considered to be positive when the level of glycosaminoglycan was above the upper level of normal for that patient's age group. While the preferred glycosaminoglycan standard employed is chondroitin-6-sulfate, other sulfated glycosaminoglycans such as heparan sulfate, can be used.

The invention will be further described by reference to the following detailed example.

EXAMPLE 1

Glycosaminoglycan Anaylsis of Urine Specimens Collected on Paper

A. Dye Reagent. A stock solution of 0.35 mM of 1,9-dimethylmethylene blue chloride (#03610- 1; Polysciences, Inc., Warrington, PA), the "10×stock solution," was made by dissolving 122 mg of dye in 10 ml of 95% ethanol which was then diluted to 1 liter with 0.2 M sodium formate buffer (pH 3.5). This 10×stock solution was stored in an amber bottle at room temperature for up to 2 months.

For analysis of urine specimens collected on filter paper, 35 uM ("1×") and 105 uM ("3×") dye solutions were prepared on the day of use by dilution of the "10×" stock solution with 0.2 M sodium formate buffer.

B. Collection of Urine Specimen. For preliminary characterization of methodologies, urine specimens were collected from normal individuals or patients with mucopolysaccharide storage diseases and stored at $-20°$ C. until assay. The urine sample was then eluted by gentle rotation of the filter paper strip in 3.5 ml of distilled water for 15-30 minutes at room temperature. Aliquots of this filter paper eluate were then assayed for glycosaminoglycan and creatinine. For mass screening, urine specimens were collected by blotting diapers with type 903 paper (#15750, Schleicher & Schuell, Inc., Keene, NH).

C. Elution of Urine Specimens. For urine specimens collected on filter paper, the sample collection paper was cut to a convenient size of 30 cm$^2$ (typically 10 cm×3 cm) which was folded accordian style and placed in a 15 ml polypropylene tube. (#2095 Falcon, Becton Dickinson Labware, Oxnard, CA 93030). For samples which had glycosaminoglycan and/or creatinine concentrations beyond the limits of linearity, an appropriately smaller piece of filter paper (typically, 3–6 cm$^2$) was eluted and assayed in the same manner.

D. Glycosaminoglycan Standards. Reference solutions of heparan sulfate from bovine kidney (#H9637; Sigma, St. Louis, MO), keratan sulfate from bovine cornea (#K3001; Sigma, St. Louis, MO), chondroitin sulfate type A from whale cartilage (#C3134; Sigma, St. Louis, MO), dermatan sulfate i.e., chondroitin sulfate type B from porcine skin; (#C4259; Sigma, St. Louis, MO), chondroitin sulfate type C from shark cartilage (#C4384; Sigma, St. Louis, MO) were prepared in distilled water and stored at $-20°$ C.

E. Dye-binding Assay for Glycosaminoglycan. For the standard assay reaction utilizing fresh or frozen urine specimens, 40 ul of sample (urine specimen from normal individuals, diluted urine specimen from MPS patients, or glycosaminoglycan reference solution) was mixed with 1.0 ml of "1×" (0.035 $\mu$m) dye reagent in plastic semi-micro spectrophotometer cuvettes (#2410, Stockwell Scientific, Walnut, CA 91789). Optical density at 535 nm was measured immediately with a Beckman DU-8 or DU-50 spectrophotometer. Absorbance at 535 nm was determined and compared to appropriate standard solutions of chondroitin-6-sulfate, 25–250 g/ml or other sulfated glycosaminoglycans. Visual assessment of color was made in standard fluorescent light and under incandescent light.

For paper eluate specimens, a 0.5 ml aliquot of paper matrix eluate was added to 0.25 ml of 3×(.105 M) dye reagent. The absorbance was determined at 535 nm and compared to standard solutions of chondroitin-6-sulfate, 1-10 ug/ml, or other sulfated glycosaminoglycans.

F. Creatinine Assay. Creatinine was determined by the method of Jaffee supra, (Bosnes and Taussky, 1945) by mixing a 0.25 ml aliquot of filter paper eluate, or diluted 1:10 eluate, with 1.0 ml of 20% saturated picric acid (1:5 dilution of saturated picric acid solution, #925-40; Sigma, St. Louis, MO) and 1.0 ml of a 0.75% w/v solution of sodium hydroxide. After reaction for 20 minutes, absorbance at 535 nm was determined and compared to appropriate creatinine standard solutions of 1, 3, 10 and 15 mg/dl (#925-11 and #925-15; Sigma, St. Louis, MO).

G. Data Management and Statistical Methods. Results were recorded on Lotus 1-2-3 (TM) version 2A which was programmed to calculate glycosaminoglycan and creatinine concentrations, and to calculate urinary glycosaminoglycan as the ratio glycosaminoglycan/creatinine (mg GAG/gm creatinine). Lotus 1-2-3 was also programmed to review data and to flag results at the extremes thus indicating insufficient urine sample (O.D. for GAG or creatinine of <0.025) and suspiciously high levels of excretion (results of >350 mg GAG/gm creatinine).

H. Development of Standard Assay Conditions. As a means of facilitating sample collection from large numbers of patients, a method of urine collection on filter paper was examined. Pieces of specimen collection paper measuring 10×10 cm were blotted with urine-stained diapers until the filter paper is thoroughly wet, or were wetted with standard solutions. Filter papers were then dried on a desk under ambient atmospheric conditions until dry.

Saturation of GAG-DMB complex formation. As an initial means of evaluating the potential useful range of glycosaminoglycan concentration, the color and absorbance of various concentrations of heparan sulfate was determined. The visible color changes and increasing O.D. were observed within the first few seconds after mixing heparan sulfate with the DMB reagent. While reference solutions of 60 ug/ml or less retained the blue color of unreacted DMB, solutions with 70-90 ug/ml appeared lavender, and the samples with 100-1000 ug/ml were brilliant pink and were prone to precipitation over time. Increasing heparan sulfate concentrations above approximately 200 ug/ml resulted in no additional increase in absorbance with a maximum of approximately 0.35 O.D. units.

Specificity of GAG-DMB complex formation. Other glycosaminoglycans were then studied in a similar fashion. The pathologically important sulfated glycosaminoglycans (heparan sulfate, keratan sulfate, chondroitin-4-sulfate, dermatan sulfate, and chondroitin-6-sulfate) exhibited the same reaction with dye. Specifically, referring to FIG. 1, as measured by change in absorbance (535 nm), the DMB reagent reacted with each of the pathologically significant glycosaminoglycans (heparan sulfate, keratan sulfate, chondroitin-4-sulfate, dermatan sulfate, chrondroitin-6-sulfate) reaching a saturation of GAG-DMB complex formation at approximately 200 ug/ml glycosaminoglycan. When presented as a semilogarithmic plot, absorbance was seen as a sigmoidal function of glycosaminoglycan concentration with the highest concentrations of each glycosaminoglycan species attaining the same maximal absorbance. Within the limits of this study, DMB exhibited the same reactivity with each of the different sulfated glycosaminoglycans. This observation is unexpectedly in contrast to previous observations that DMB was less

Inertness of Filter Paper to Dye.

Direct application of DMB dye reagent to filter paper resulted only in the blue color of unreacted dye, and showed no change to the violet color of DMB-GAG complexes. The eluate from filter papers was mixed with 1 ml of dye reagent and found to yield no visible color change, and no absorbance by spectrophotometry. Therefore, it appears that virgin specimen collection paper does not react with DMB dye under these conditions.

Time Course of Elution of Solutes from a Paper Matrix.

Figure 2:
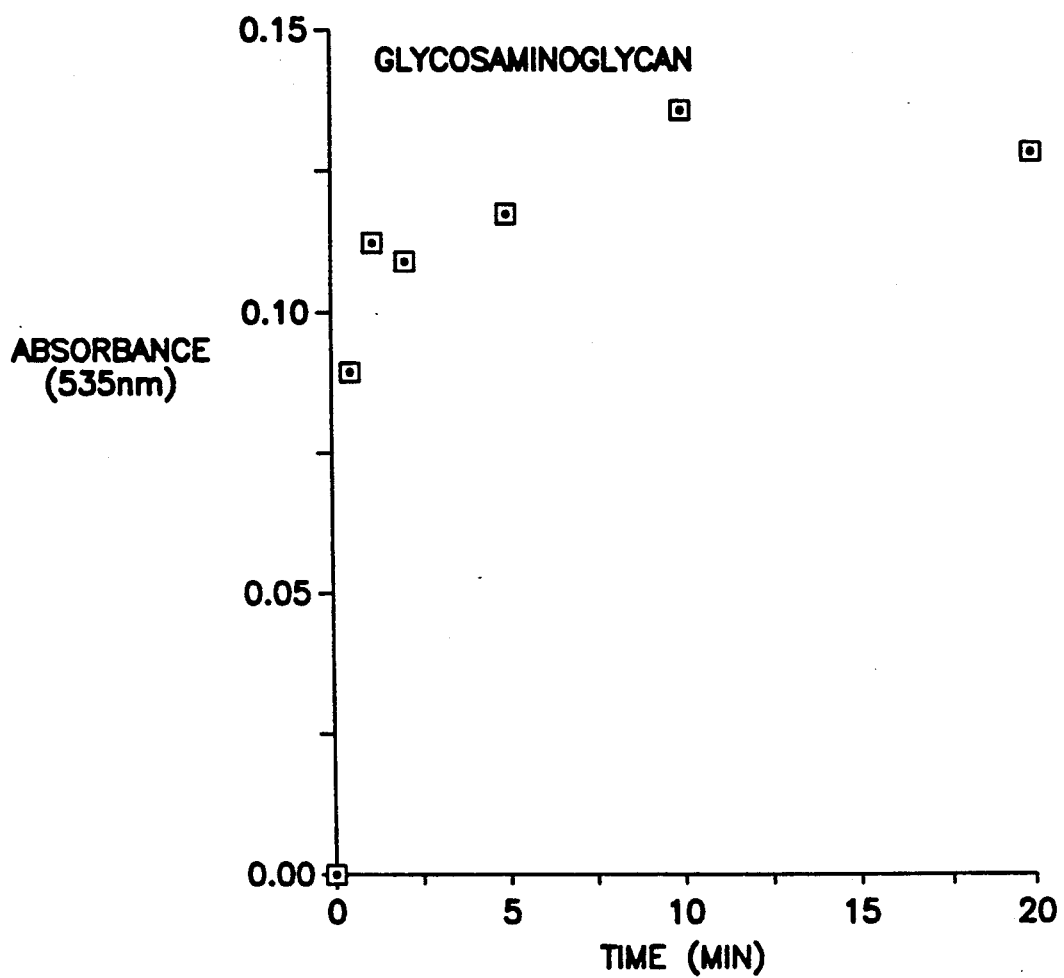
FIGS. 2 and 3 show a time course for elution of glycosaminoglycan and creatinine in water from specimen collection paper.
Figure 3:
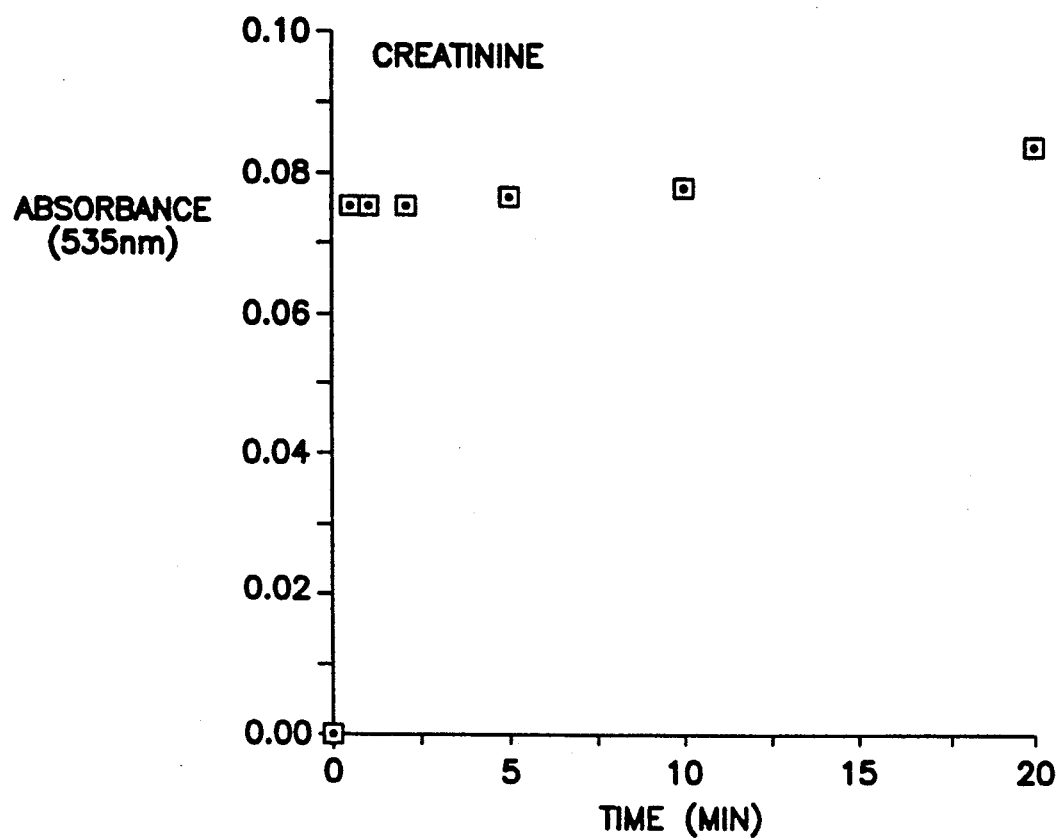

To determine if glycosaminoglycan and creatinine could be recovered from a convenient, porous collection and transport medium, solutions of chondroitin-6-sulfate and creatinine were applied to $3 \times 10$ cm$^2$ pieces of specimen collection paper, dried overnight, and then eluted for selected times in distilled water. As seen in FIGS. 2 and 3, of the time course of elution, it appears that both glycosaminoglycan and creatinine were maximally eluted within 10 minutes. Creatinine was more rapidly soluble being maximally eluted within 1-2 minutes, while chondroitin-6-sulfate was more slowly removed into solution.

Interference of Salts with DMB-GAG Reaction..

To achieve more complete recovery of glycosaminoglycan, the conditions of elution solvent were modified with respect to pH and ionic strength. As shown in Table 1, increasing concentrations of either sodium formate buffer or sodium chloride altered DMB-GAG interactions resulting in increased absorbance and rapid precipitation of DMB-GAG complexes. Increased salt concentration also was associated with a change in visible color to a marine blue not seen in the absence of salt. These changes largely prohibited alteration of the eluting solution with respect to salt concentration.

TABLE 1

Effect of Salt Concentration on the Optical Density of DMB and GAG-DMB Complexes*

| Eluate NaCl concentration | "Blank" eluate* (O.D.) | Glycosaminoglycan** Standard (O.D.) | | Predicted*** (O.D.) |
|---|---|---|---|---|
| 0% | .000 | .126 | .130 | .200 |
| 1% | .029 | .168 | .180 | " |
| 2% | .048 | .190 | .215 | " |
| 3% | −.062 | .233 | .232 | " |
| 4% | .025 | .265 | .247 | " |

*A piece of virgin specimen collection paper (3 × 10 cm) was eluted with 3.5 ml of the specified concentrations of NaCl in water), and then mixed with DMB dye reagent in the standard assay. Salt concentration had a negligible effect on DMB dye alone ("Blank" eluate).
**Glycosaminoglycan reference solution (1 ml of 20 g/ml chondroitin-6-sulfate was dried on 3 × 10 cm pieces of paper matrix. Each specimen was then eluted in 3.5 ml of distilled water containing the specified salt concentration, and then assayed for glycosaminoglycan by addition of DMB dye reagent in the standard assay. Increasing concentrations of NaCl in the eluate solution produced increased optical density such that measured O.D. was higher than attributable to GAG-DMB complexes alone (each number represents the mean of 3 determinations on each reference sample applied to a piece of paper matrix.)
***Optical density predicted from 100% recovery of applied specimen (20 g chondroitin-6-sulfate) assayed without NaCl. Quantitative Recovery of Glycosaminoglycan from a Paper Matrix.

Figure 4:
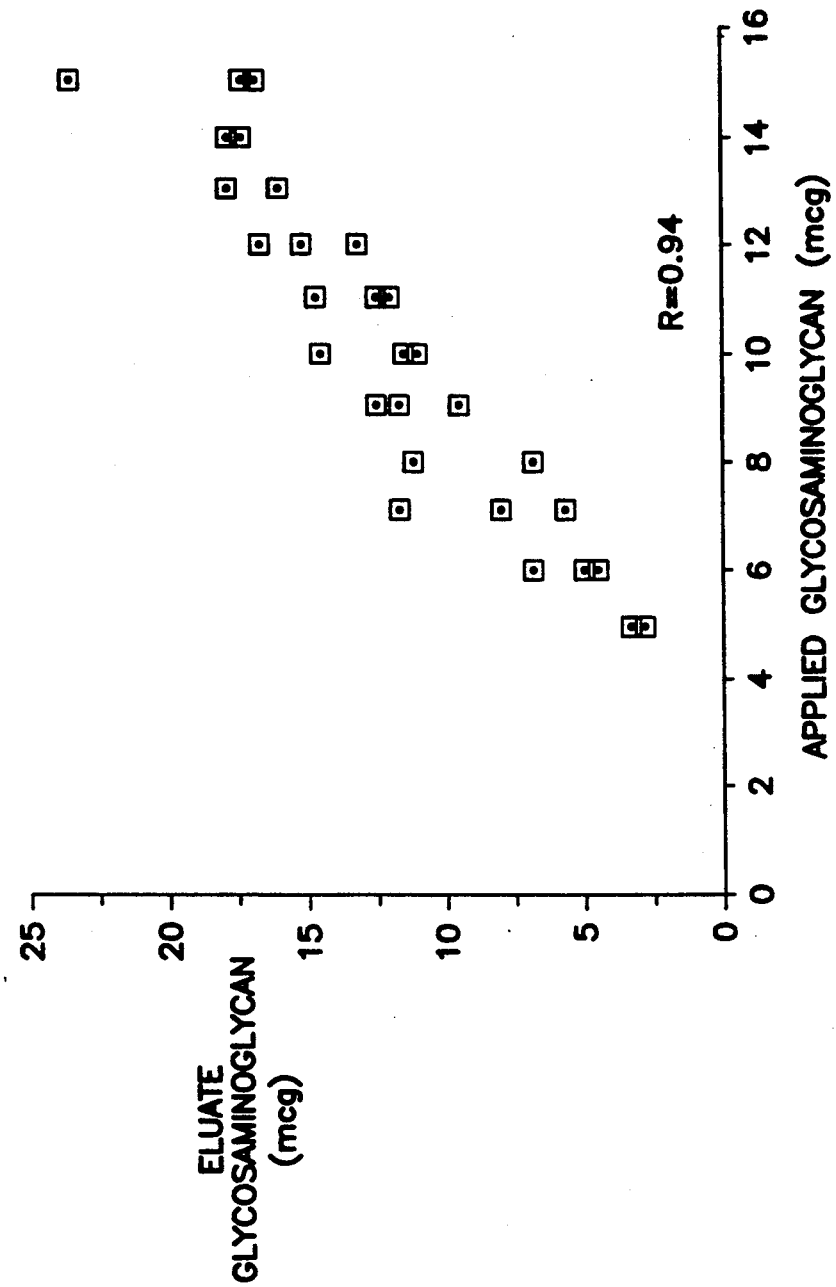
FIG. 4 shows extraction of chondroitin-6-sulfate from specimen collection paper.

Recovery of GAG standard solutions from filter paper was studied. Standard solutions of chondroitin-6-sulfate were applied to 3 cm × 10 cm filter paper strips, dried, and then eluted in 3.5 ml of distilled water. As shown in FIG. 4, extraction of chondroitin-6-sulfate was found to be proportional to the amount applied (correlation coefficient of 0.94). As a means of providing an internal physiologic standard, extraction of creatinine standards was studied in a similar fashion and extraction of creatinine was found to be quantitative.

Application of Assay to Human Urine Specimens Human Urine Specimen.

Figure 5:
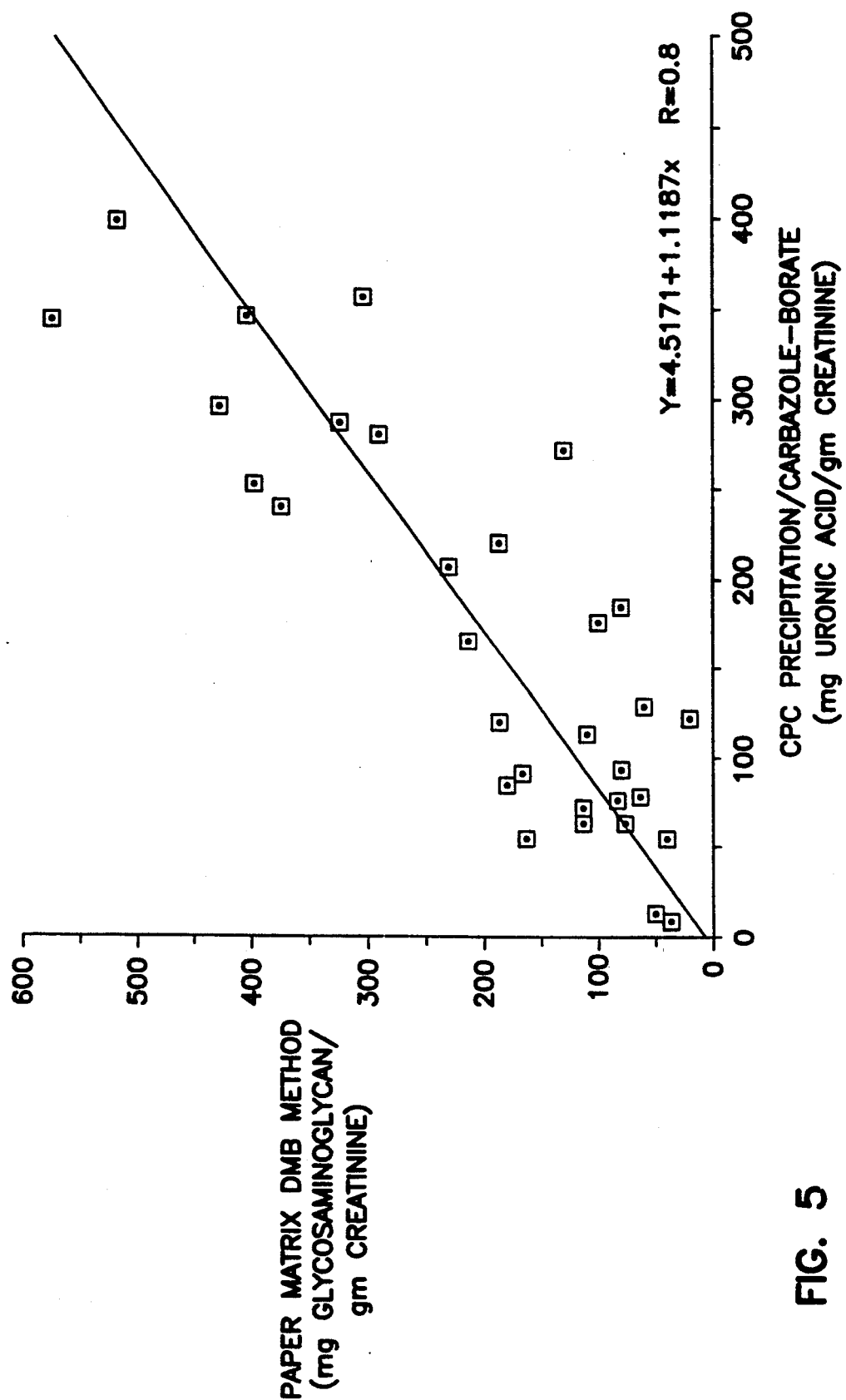
FIG. 5 shows comparison of methods for quantitation of urinary glycosaminoglycan. Paper Matrix DMB Method vs. Quantitation of Precipitable Uronic Acid (Carbazole-Borate).

Patient urine samples were blotted and studied in this fashion, and compared to quantitation of GAG and creatinine determined in the same specimens assayed studied by the CPC/carbazole-borate method (FIG. 5).

Quantitation of Urinary Glycosaminoglycan Excretion in Normal Newborns.

Figure 6:
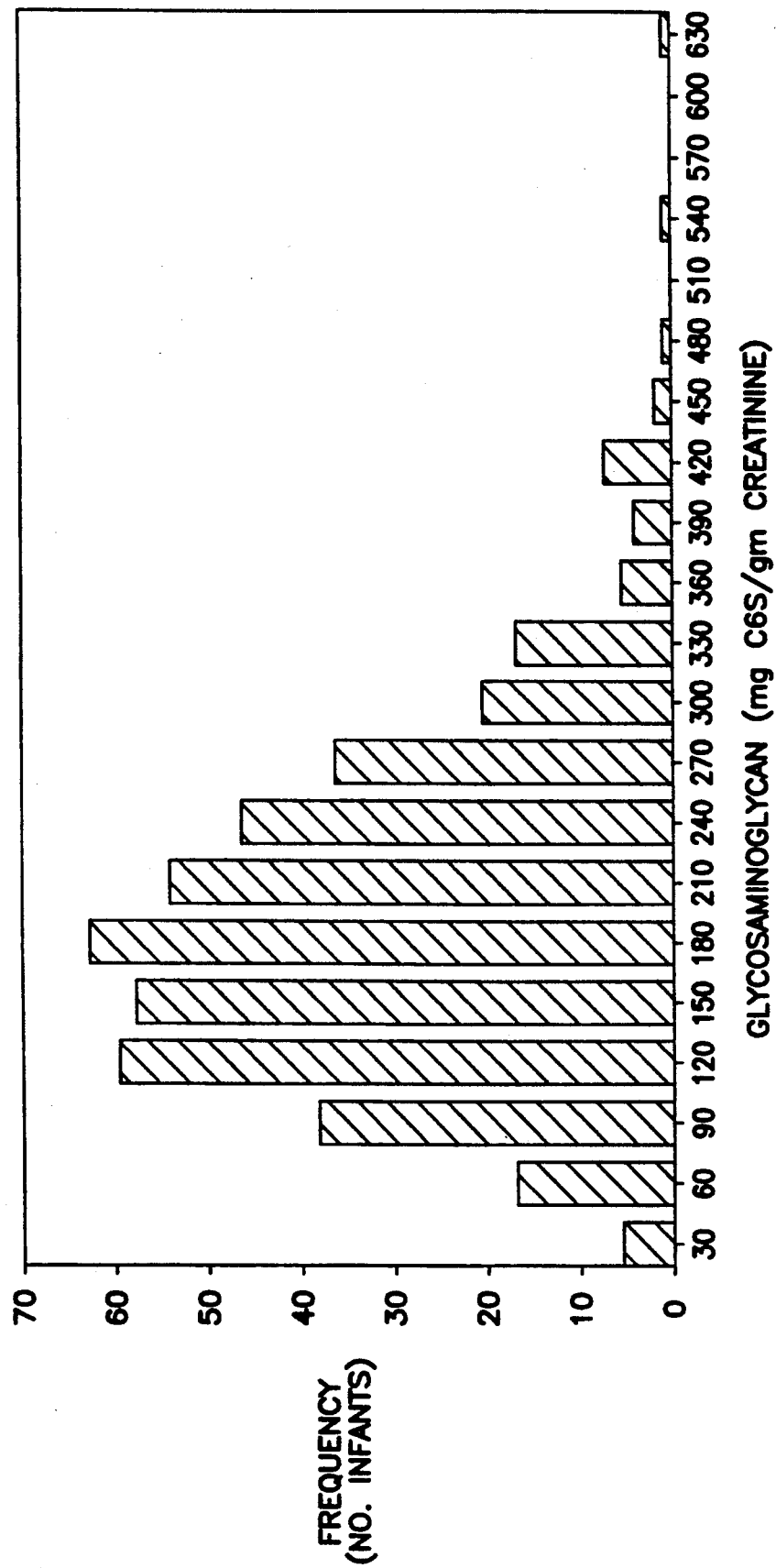
FIG. 6 shows distribution of glycosaminoglycan excretion in normal newborn infants.

To evaluate the applicability of this method to testing of a large number of specimens collected from newborn infants, and to determine the range of glycosaminoglycan excretion in the population, the method was applied to a specimen collected from 435 newborn infants. As seen in FIG. 6, the frequency distribution has a mean of 179 mg GAG/gm creatinine (standard deviation 86.3).

Rapid Quantitation of Urinary Glycosaminoglycan Excretion in MPS.

As seen in Table 2, patients with the spectrum of MPS have elevated levels of glycosaminoglycan excretion. Although there would appear to be some overlap between the older patients with MPS, and the normal newborn population, it is believed that newborns with MPS will have higher levels of GAG/creatinine as indicated by other methodologies (Huang K.-C, et al., Clin. Chim. Acta., 151:141-146, 1985), and that this test should readily identify most, if not all, affected MPS infants dependent upon what quantitative criteria are used to discriminate positive and negative test results.

TABLE 2

Rapid Quantitation of Glycosaminoglycan Excretion in Urine Samples Collected, Dried, and Mailed on Specimen Collection Paper from Patients with Mucopolysacchardosis.

| Patient | Age at Test (yrs) | Urinary Glycosaminoglycan (mg C6S/gm creatinine) | |
|---|---|---|---|
| | | individual samples | mean |
| Hurler Syndrome (MPS type I-H) | | | |
| 1 | 1.0 | 520 | 520 |
| 2 | 1.0 | 627 | 627 |
| 3 | 1.0 | 119, 344 | 232 |
| 4 | 2.0 | 1997, 600 | 1299 |
| 5 | 2.0 | 928, 1613 | 1271 |
| 6 | 3.0 | 447, 707 | 577 |
| 7 | 3.0 | 798 | 798 |
| 8 | 5.0 | 948, 1493 | 1221 |
| 9 | 8.0 | 533, 682 | 608 |
| Hunter Syndrome (MPS type II) | | | |
| 1 | 3.0 | 454, 331, 394 | 393 |
| 2 | 7.0 | 506 | 506 |
| Sanfilippo syndrome (MPS type III) 1 | 7.0 | 194, 247 | 221 |
| Maroteaux-Lamy syndrome (MPS type VI) 1 | 8.0 | 860, 733 | 797 |

EXAMPLE 2

Application of Direct DMB Method to Monitor Therapeutic Response in Liquid Urine Specimens.

Figure 7:
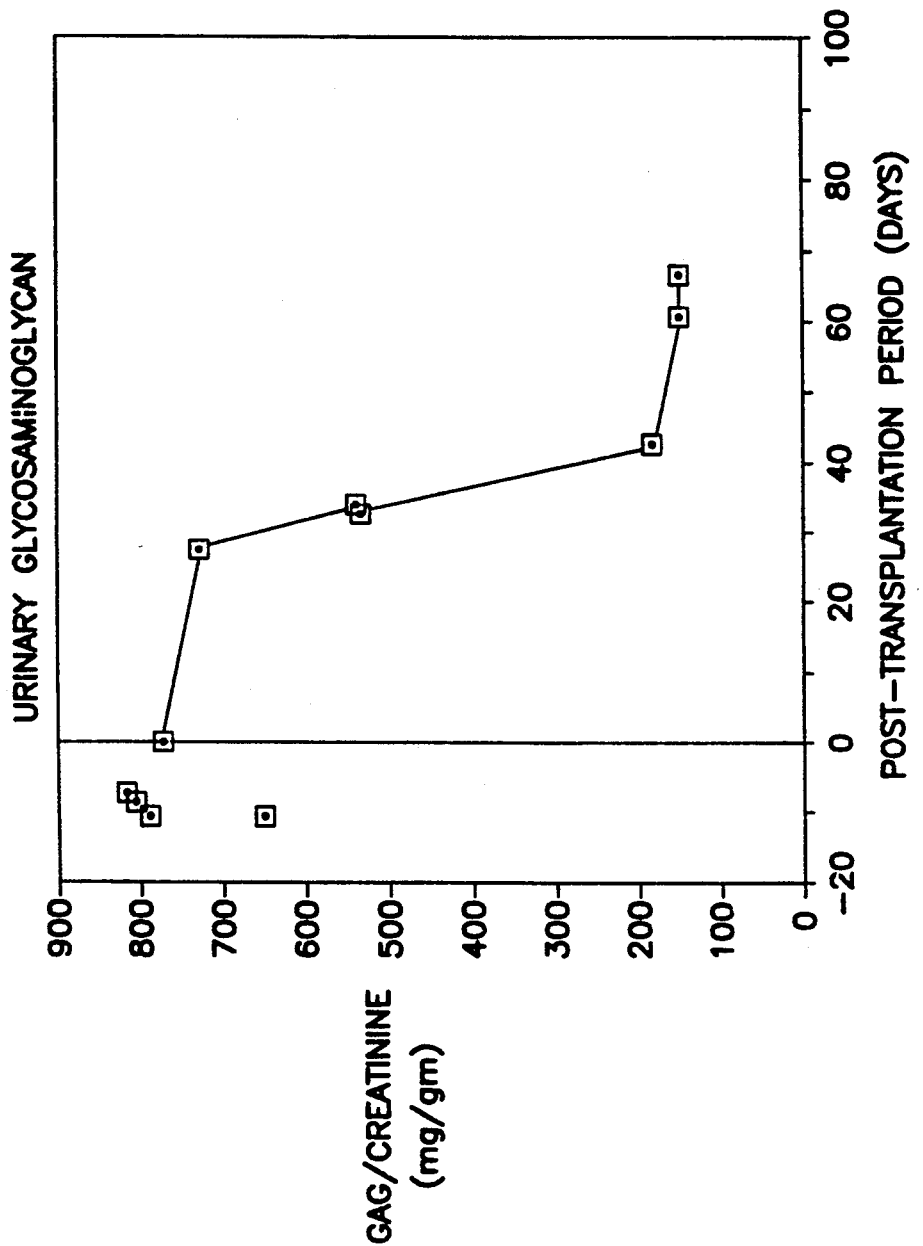
FIG. 7 shows urinary GAG levels in a child with Hurler's syndrome before and after bone marrow transplant as measured by dye-binding assay for glycosaminoglycan.

FIG. 7 illustrates application of "direct DMB" method for diagnosis of mucopolysaccharidosis, and to monitor the progress of treatment by bone marrow transplantation. Five small liquid urine specimens (approximately 1 ml each) were obtained from a 1-year-old girl with the suspected diagnosis of Hurler syndrome (MPS type I), and were then transported to our laboratory in a frozen state (by overnight express delivery on dry ice from Dr. P. Jean Henslee, Bone Marrow Transplantation Program, University of Kentucky, Lexington, KY.) When tested by the direct DMB method, see Example 1 (A,D-F), the 5 liquid specimens were found to have pathologically elevated levels of glycosaminoglycan (650–850 mg glycosaminoglycan/gm creatinine) thus confirming the suspected diagnosis of lethal MPS disease in this child.

Following this little girl's bone marrow transplant (on "Day 0"), additional samples were obtained, frozen, and transported on dry ice by express mail to our laboratory. As illustrated in FIG. 7, declining levels of urinary glycosaminoglycan after transplant (from "Day 0" to "Day 78") were the first indications of metabolic correction, i.e., successful treatment. Drugs administered to patients during bone marrow transplantation, and excreted in urine, do not interfere with the direct DMB method of quantitating urinary glycasminoglycan.

Comparison of direct DMB method to conventional methods.

To have monitored this patient's response to transplantation therapy by conventional laboratory methods would have required larger urine specimens (difficult to collect specimens of 10–15 ml), and an elaborate and expensive two-day laboratory procedure. In contrast, these results (FIG. 5) were obtained on readily available 1 ml urine specimens, and in less than 4 hours, utilizing the new direct DMB method.

The unique contributions of the present invention are the development of methods for: 1) direct quantitation of urine glycosaminoglycan, without prior isolation or separation from other urine constituents, in fresh/frozen liquid specimens, and 2) eluting and sensitive quantitation of very small amounts of glycosaminoglycan from a paper matrix collection system.

Large numbers of specimens can readily be collected and conveniently transported to central testing facilities, employing the method of the present invention with paper matrix collection. Collection of urine samples on a paper matrix should facilitate a similar monitoring capability, but without the requirement of expensive overnight express delivery of frozen urine specimens shipped on dry ice (typical charges for express delivery of frozen specimens are $35 to $75 per specimen.) Specimens absorbed and dried on a paper matrix can be transported for 25 cents postage (plus the cost of a plastic bag and paper envelope.) The method of analysis is rapid with a specimen turnover time of less than one hour. A single specimen is available for repeat analysis if further validation or checking is desirable. The actual quantitative assay requires inexpensive reagents that are stable for storage at room temperature without special precautions. In combination, these features make the present invention readily adaptable to automation.

Nevertheless, manual techniques were used in a pilot study to rapidly screen several hundred specimens. In contrast to existing screening methods which are semi-quantitative, this is a precisely quantitative technique and thereby provides a means for defining specific false-positive and false-negative rates based on population information, and which can be varied depending upon the requirements and facilities of any particular screening program.

With the present invention, it is believed that all newborn infants could be tested for MPS on a regular basis. Earlier detection and definitive diagnosis of children with MPS conditions will facilitate more efficient and specific clinical management, obviate more elaborate clinical evaluation of associated abnormalities and symptoms, permit earlier genetic counseling regarding future pregnancies, and permit earlier presymptomatic treatment by bone marrow transplantation.

It is believed that the method described herein can be adapted for direct visual inspection of a sample for mucopolysaccharide storage diseases. Such a direct measurement would involve extracting a sample of the patient's urine which has been absorbed onto a porous sheet and dried, by agitating said sheet with water for a period of time sufficient to yield an aqueous extract which contains glycosaminoglycan; adding a known amount of 1,9-dimethylmethylene blue chloride dye reagent to at least a portion of the aqueous extract to produce a test solution; and inspecting the solution for color change indicative of the presence of mucopolysaccharide storage diseases. The color change in the sample can be compared with standard color strips reflecting information for normal urine glycosaminoglycan.

The invention has been described with reference to various specific and preferred embodiments and techniques. However, it should be understood that many variations and modifications may be made while remaining within the spirit and scope of the invention.

What is claimed is:

1. A method for the screening of mucopolysaccharide storage diseases in a human patient consisting essentially of:

(a) extracting a sample of the patient's urine which has been absorbed onto a porous sheet and dried, by agitating said sheet with water for a period of time sufficient to yield an aqueous extract which contains glycosaminoglycan and creatinine;

(b) determining the amount of creatinine in a first portion of said aqueous extract, said amount of creatinine being normalized to standard creatinine reference solutions;

(c) adding a known amount of 1,9-dimethylmethylene blue chloride dye reagent to a second portion of said aqueous extract without prior separation of urine constituents from said extract to produce a test solution, said test solution having sufficient buffer to stabilize glycosaminoglycan-dye complexes in solution without precipitation;

(d) determining the amount of glycosaminoglycan in said test solution by inspection of color change in said test solution, said amount of glycosaminoglycan being normalized to a standard glycosaminoglycan solution;

(e) calculating urinary glycosaminoglycan in said sample as a ratio of normalized glycosaminoglycan to normalized creatinine; and (f) comparing the urinary glycosaminoglycan in said sample to control levels of urinary glycosaminoglycan.

2. The method of claim 1 wherein said 1,9-dimethylmethylene blue dye reagent contains from about 0.05 M to about 0.25 M sodium formate buffer to stabilize glycosaminoglycan-dye complexes in solution without precipitation.

3. The method of claim 1 wherein said glycosaminoglycan in said standard glycosaminoglycan solution is a sulfated glycosaminoglycan selected from the group consisting of chondroitin-6-sulfate, heparan sulfate, keratan sulfate, and dermatan sulfate.

4. The method of claim 1 wherein said 1,9-dimethylmethylene blue dye reagent is from about 0.05 mM to about 0.20 mM.

5. The method of claim 1 wherein the patient is less than one year old.

6. The method of claim 1 wherein the porous sheet is a piece of paper.

7. The method of claim 1 wherein said control level of urinary glycosaminoglycan is 50–350 mg glycosaminoglycan/g creatinine, for newborn infants.

8. The method of claim 1 wherein said inspection of said test solution is conducted with a spectrophotometer measuring optical density at about 530 to 540 nm.

9. The method of claim 1 wherein said extracting of said sample is conducted for about 5 to about 15 minutes.

10. The method of claim 1 wherein the screening is accomplished by comparing the normalized amounts of glycosaminoglycan determined in step (d) which are derived from a single sample of urine to normalized glycosaminoglycan levels representative of an age-matched human individual who excretes normal amounts of glycosaminoglycan.

* * * * *